US012605360B2

(12) United States Patent (10) Patent No.: US 12,605,360 B2
Dattatreya et al. (45) Date of Patent: Apr. 21, 2026

(54) COMPOSITIONS AND METHODS USING XANTHAN GUM TO STABILIZE AT LEAST ONE UROLITHIN IN AN AQUEOUS MATRIX

(71) Applicant: SOCIETE DES PRODUITS NESTLE S.A., Vevey (CH)

(72) Inventors: Anupama Dattatreya, Skillman, NJ (US); Vivek Dilip Savant, Bridgewater, NJ (US); Loretta Grant, Middlesex, NJ (US); Sanjay Gupta, Belle Mead, NJ (US)

(73) Assignee: Societe des Produits Nestle S.A., Vevey (CH)

( * ) Notice: Subject to any disclaimer, the term of this patent is extended or adjusted under 35 U.S.C. 154(b) by 444 days.

(21) Appl. No.: 18/246,442

(22) PCT Filed: Sep. 22, 2021

(86) PCT No.: PCT/EP2021/076099
§ 371 (c)(1),
(2) Date: Mar. 23, 2023

(87) PCT Pub. No.: WO2022/063846
PCT Pub. Date: Mar. 31, 2022

(65) Prior Publication Data
US 2023/0372291 A1 Nov. 23, 2023

Related U.S. Application Data

(60) Provisional application No. 63/083,383, filed on Sep. 25, 2020.

(51) Int. Cl.
*A61K 31/366* (2006.01)
*A61K 9/00* (2006.01)
*A61K 9/16* (2006.01)

(52) U.S. Cl.
CPC .......... *A61K 31/366* (2013.01); *A61K 9/0053* (2013.01); *A61K 9/0092* (2013.01); *A61K*

*9/1617* (2013.01); *A61K 9/1652* (2013.01); *A61K 9/1664* (2013.01)

(58) Field of Classification Search
CPC .................................................... A61K 31/366
See application file for complete search history.

(56) References Cited

U.S. PATENT DOCUMENTS

2019/0255017 A1* 8/2019 Kalidindi ............... A61K 31/37

FOREIGN PATENT DOCUMENTS

| CN | 110709077 A | 1/2020 |
| JP | 2009278970 A | 12/2009 |
| JP | 2017218434 | 12/2017 |
| WO | 2007133249 | 11/2007 |
| WO | 2017135286 | 8/2017 |

OTHER PUBLICATIONS

Chinese Office Action for Appl No. 202180050772.4 dated Feb. 6, 2025, 8 pages.
Japanese Office Action for App. No. 2023-517355 dated Sep. 30, 2025 (6 pages).

* cited by examiner

*Primary Examiner* — Rei Tsang Shiao
(74) *Attorney, Agent, or Firm* — K&L Gates LLP

(57) ABSTRACT

A powder contains xanthan gum and at least one urolithin, such as Urolithin A; and the powder can be reconstituted in a liquid such as water to form a liquid composition for oral consumption, such as a beverage. The xanthan gum can keep the majority of the at least one urolithin in suspension in the beverage. The resultant liquid composition for oral consumption is another aspect of the present disclosure, as well as methods of making the powder, making the liquid composition for oral consumption, and using the powder or liquid composition prophylactically or therapeutically.

13 Claims, 22 Drawing Sheets

Effect of different stabilizers on the suspension of UA in water (no acid)

| S. No. | Stabilizer | pH | Viscosity | Easy to dissolve? UA suspended well? | Mouthfeel | Taste | Sample Prep | Picture |
|---|---|---|---|---|---|---|---|---|
| 1 | Xanthan | 6.91 | Spindle 61 30 rpm–169.2cp 60 rpm–ee Spindle 62 60 rpm–121.1cp | Xanthan dissolves easily, and it keeps UA suspended very well. | full body thicker mouthfeel | Clean H2O taste | 1.43 g Base + 0.55 g gum dissolved in 8 fl oz water | |
| 2 | Acacia | 6.87 | Spindle 61 30 rpm- 1.40cp 60 rpm- 2.10cp | Acacia gum dissolved well, but it does not keep UA suspended in the solution | thin liquid mouthfeel | Clean H2O taste | 1.43 g Base + 0.55 g gum dissolved in 8 fl oz water | |
| 3 | Gellan | 7.06 | Spindle 61 30 rpm-1.60 60 rpm-2.30cp | Gellan gum dissolved well, but it does not keep UA suspended in the solution. | thin liquid mouthfeel | Clean H2O taste | 1.43 g Base + 0.55 g gum dissolved in 8 fl oz water | |
| 4 | Guar | 7.12 | Spindle 61 30 rpm - 6.60cp 60 rpm- 8.30cp | Guar gum dissolved easily, It seems to keep some UA particles suspended, but a lot of UA particles still fell to the bottom of the cup. | slightly thicker mouthfeel | Starchy offnote | 1.43 g Base + 0.55 g gum dissolved in 8 fl oz water | |

After mixing in water. Wait for 5 min, mix again and then measure viscosity. This allows some time to thicken.

FIG. 3B

Effect of different stabilizers on the suspension of UA in water (no acid)

| S. No. | Stabilizer | pH | Viscosity | Easy to dissolve? UA suspended well? | Mouthfeel | Taste | Sample Prep | Picture |
|---|---|---|---|---|---|---|---|---|
| 5 | PHGG | 7.09 | Spindle 61 30 rpm -1.40cp 60 rpm- 1.80cp | PHGG does not dissolve well. PHGG floated to the bottom of the cup. | thin liquid mouthfeel | Clean H2O taste | 1.43 g Base + 0.55 g gum dissolved in 8 fl oz water | |
| 6 | FMC Blend | 7.22 | Spindle 61 30 rpm-1.80cp 60 rpm-2.10cp | FMC Blend dissolved well, but it was unable to keep UA suspended in the solution. | thin liquid mouthfeel | Clean H2O taste | 1.43 g Base + 0.55 g gum dissolved in 8 fl oz water | |
| 7 | Blend of Guar and Xanthan | 6.83 | Spindle 62 30 rpm-245.9cp 60 rpm-164.5cp | Xanthan and guar gum dissloved easily, and it was able to keep UA suspended in the solution. | full body thicker mouthfeel | Starchy offnote | 1.43 g Base + 0.50 g guar + 0.25g Xanthan and then dissolved in 8 fl oz water | |

After mixing in water. Wait for 5 min, mix again and then measure viscosity. This allows some time to thicken.

FIG. 4A

Effect of different stabilizers on the suspension of UA in water in presence of acid

| S. No. | Stabilizer | pH | Viscosity | Easy to dissolve? UA suspended well? | Mouthfeel | Taste | Sample Prep | Picture |
|---|---|---|---|---|---|---|---|---|
| 1 | Xanthan | 2.57 | Spindle 61 30 rpm 122.8cp 60 rpm 86.8cp | Gum was easy to dissolve, UA was suspended really well | full body, thicker mouthfeel | sour and acidic, but the gum had a clean taste | 2.23 g Base + 0.55 g gum dissolved in 8 fl oz water | |
| 2 | Acacia | 2.61 | Spindle 61 30 rpm 1.90cp 60 rpm 2.10cp | Acacia dissolved well, but the acacia gum was unable to keep the UA suspended | slightly thicker mouthfeel | sour and acidic, but the gum had a clean taste | 2.23 g Base + 0.55 g gum dissolved in 8 fl oz water | |
| 3 | Gellan | 2.4 | Spindle 61 30 rpm 1.40cp 60 rpm 2.30cp | Gellan gum dissolved well, the citric acid seemed to be breaking the gum. It was not able to keep UA suspended | thin liquid mouthfeel | sour and acidic, but the gum had a clean taste | 2.23 g Base + 0.55 g gum dissolved in 8 fl oz water | |
| 4 | Guar | 2.41 | Spindle 61 30 rpm 3.60cp 60 rpm 9.20cp | Guar gum dissolved well. Acid seemed to be the breaking gum, gel like substance around the cup. The gum was unable to keep UA suspended | thin liquid mouthfeel | sour, acidic, and starchy taste | 2.23 g Base + 0.55 g gum dissolved in 8 fl oz water | |

After mixing in water. Wait for 5 min, mix again and then measure viscosity. This allows some time to thicken.

FIG. 4B

Effect of different stabilizers on the suspension of UA in water in presence of acid

| S. No. | Stabilizer | pH | Viscosity | Easy to dissolve? UA suspended well? | Mouthfeel | Taste | Sample Prep | Picture |
|---|---|---|---|---|---|---|---|---|
| 5 | PHGG | 2.43 | Spindle 61 30 rpm 0.80CP 60 rpm 1.90 CP | PHGG did not dissolve well, it was at the bottom of the cup. Did not keep UA in suspension | thin liquid mouthfeel | sour and acidic, but the gum had a clean taste | 2.23 g Base + 0.55 g gum dissolved in 8 fl oz water | |
| 6 | FMC Blend | 2.44 | Spindle 61 30 rpm 0.80cp 60 rpm 1.60cp | Dissolved well, but did not keep UA suspended | thin liquid mouthfeel | sour and acidic, but the gum had a clean taste | 2.23 g Base + 0.55 g gum dissolved in 8 fl oz water | |
| 7 | Blend of Guar and Xanthan | 2.53 | Spindle 61 30 rpm 75.2 60 rpm 63.8 | Acid seemed to be breaking the gum, gel like substance around the cup. Kept UA suspended pretty well, but the higher level of xanthan alone, was better at keep UA suspended | full body, thicker mouthfeel | sour, acidic, and starchy taste | 2.23 g Base + 0.50 g guar + 0.25g Xanthan and then dissolved in 8 fl oz water | |

After mixing in water. Wait for 5 min, mix again and then measure viscosity. This allows some time to thicken.

FIG. 5

Effect of different levels of Xanthan on UA Suspension

| S.No | Stabilizer | pH | Viscosity | Easy to dissolve? UA suspended well? | Mouthfeel | Taste | Sample Prep | Picture |
|---|---|---|---|---|---|---|---|---|
| 1 | Xanthan (0.45g/svg) | 3,79 | Spindle 61 30rpm-62.0cp 60rpm-75.5cp | At this level, the gum was not able to hold some of the UA or magnesium phosphate in suspension | mouthfeel seemed thinner | tasted slightly sweet/ with a nice citrus flavor, the decreased gum level did not have an impact on taste | 4g FP + 8 fl oz. water | |
| 2 | Xanthan (0.55g/svg) | 3,87 | Spindle 61 30rpm-81.1cp 60rpm-82.0cp | At this level, the gum was able to hold most of the UA in suspension | Seemed to have a thicker mouthfeel | tasted slightly sweet/ with a nice citrus flavor | 4g FP + 8 fl oz water | |
| 3 | Xanthan (0.65g/svg) | 3,72 | Spindle 61 30rpm-83.0cp 60rpm-87.5cp | At this level, the gum was able to hold most of the UA in suspension | Seemed to have a thicker mouthfeel | tasted slightly sweet/ with a nice citrus flavor, the increased gum level did not have an impact on taste | 4g FP + 8 fl oz water | |

FIG. 6A
Lemon UA FOC 1 after 5 minutes
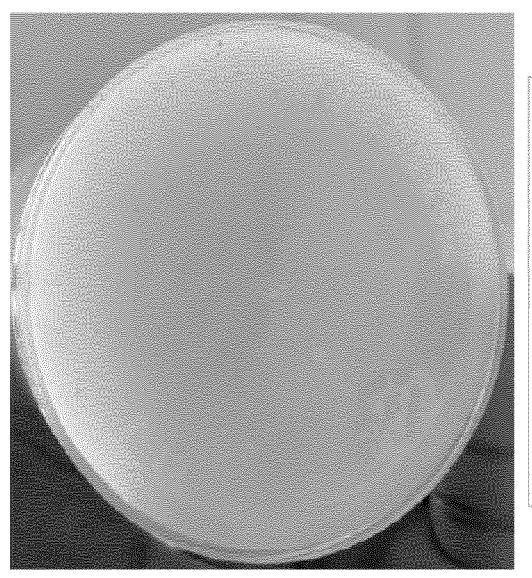
Lemon UA FOC 1 Initial: UA suspended after 4 minutes of mixing

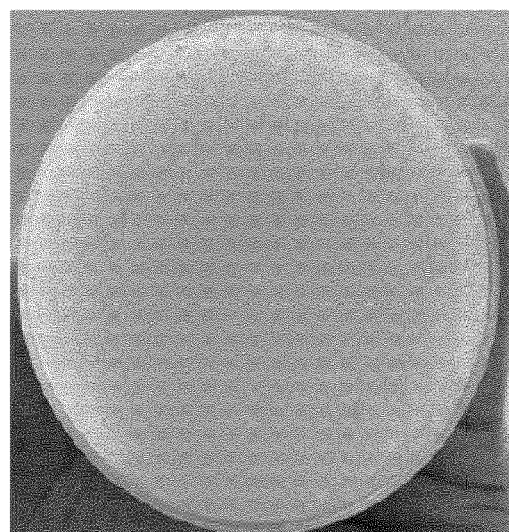
Lemon UA FOC 2 after 5 minutes
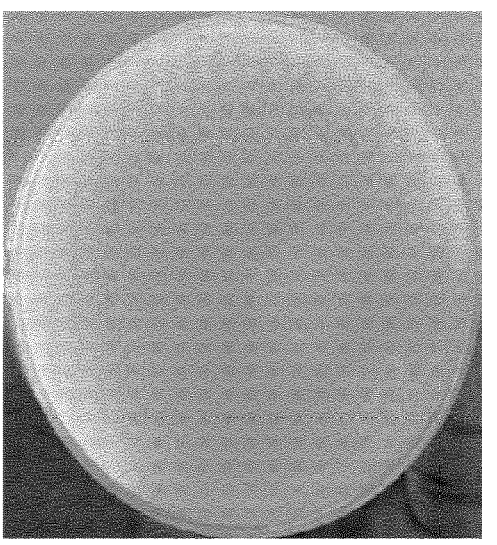
Lemon UA FOC 2 Initial: UA suspended after 4 minutes of mixing
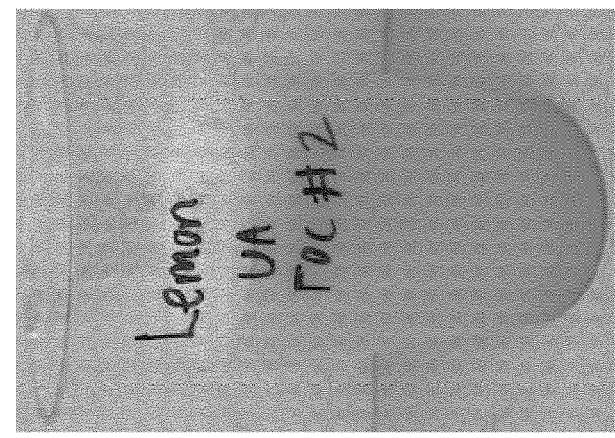
FIG. 6B

FIG. 6C
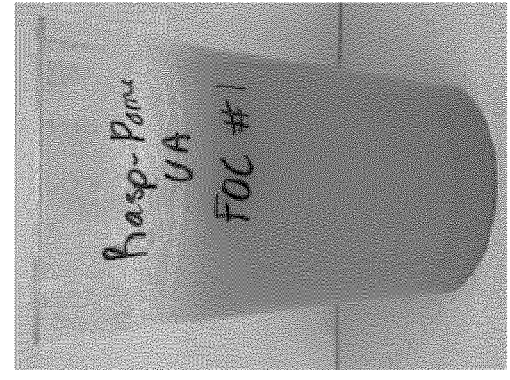
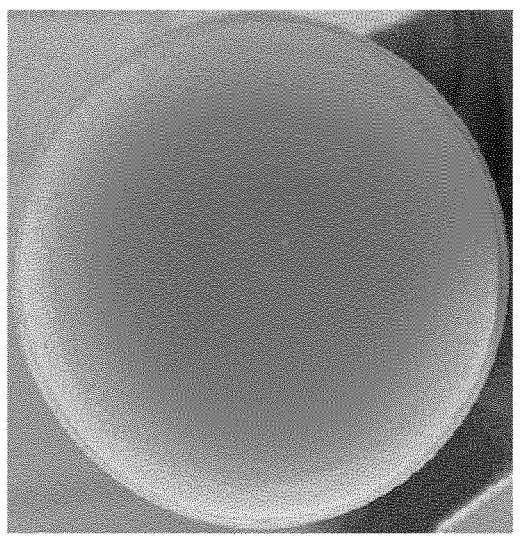
Rasp-Pome UA FOC 1 Initial: UA suspended after 4 minutes of mixing
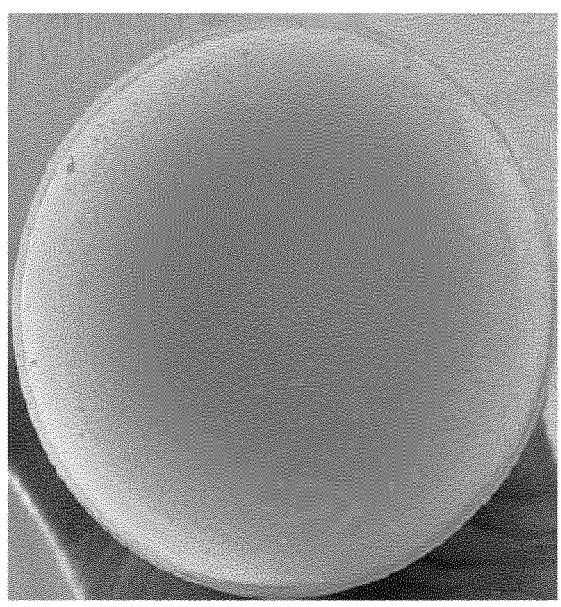
Rasp-Pome UA FOC 1 after 5 minutes

FIG. 6D
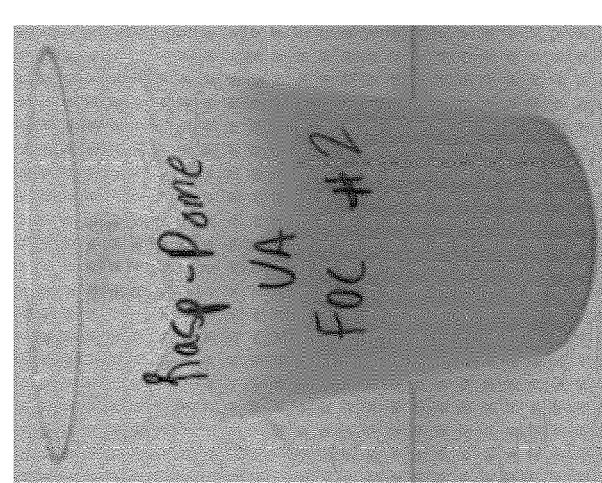
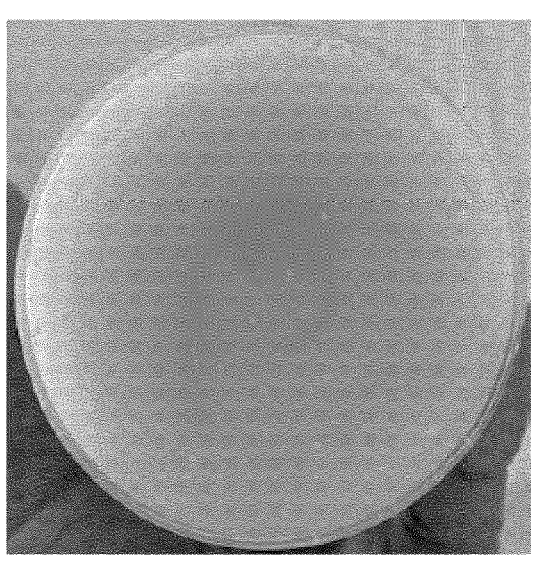
Rasp-Pome UA FOC 2 Initial: UA suspended after 4 minutes of mixing
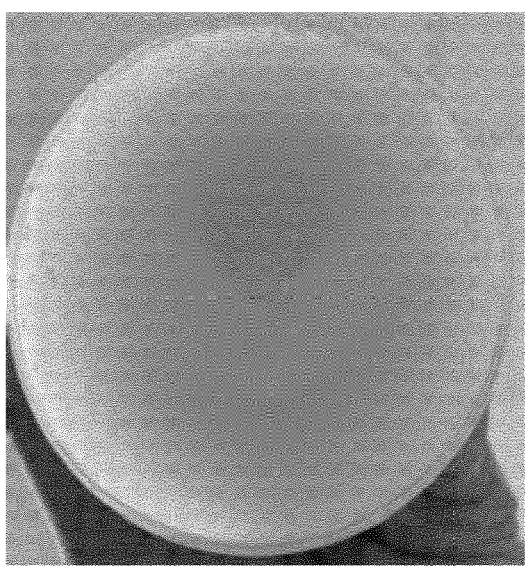
Rasp-Pome UA FOC 2 after 5 minutes Fig. 7 –Suspension of Urolithin A in different milk-based beverages in presence of Xanthan gum

Figure 7:
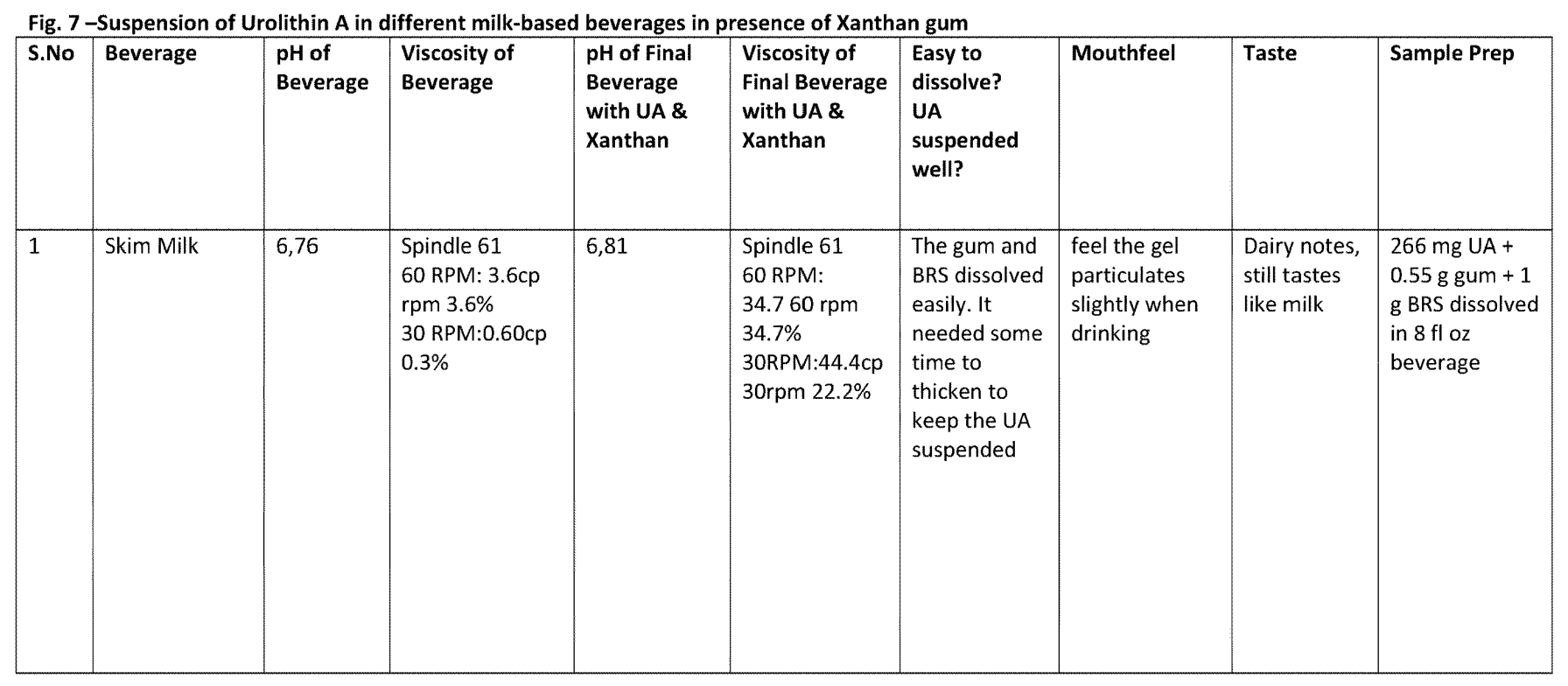

| S.No | Beverage | pH of Beverage | Viscosity of Beverage | pH of Final Beverage with UA & Xanthan | Viscosity of Final Beverage with UA & Xanthan | Easy to dissolve? UA suspended well? | Mouthfeel | Taste | Sample Prep |
|------|----------|----------------|------------------------|-----------------------------------------|------------------------------------------------|--------------------------------------|-----------|-------|-------------|
| 1 | Skim Milk | 6,76 | Spindle 61 60 RPM: 3.6cp rpm 3.6% 30 RPM:0.60cp 0.3% | 6,81 | Spindle 61 60 RPM: 34.7 60 rpm 34.7% 30RPM:44.4cp 30rpm 22.2% | The gum and BRS dissolved easily. It needed some time to thicken to keep the UA suspended | feel the gel particulates slightly when drinking | Dairy notes, still tastes like milk | 266 mg UA + 0.55 g gum + 1 g BRS dissolved in 8 fl oz beverage |

Fig. 7 Cntd

| | | | | | | | | |
|---|---|---|---|---|---|---|---|---|
| 2 | Whole Milk w/o BRS | N/A | N/A | N/A | N/A | N/A | N/A | N/A |
| 3 | Whole Milk 1.0 gram BRS | 6,72 | Spindle 61 60 RPM: 4.9 cp 4.9% 30 RPM:4.0 cp 2.0% | 6,74 | Spindle 61 30RPM: 41.6cp 20.8% 60RPM: 40.1cp 40.1% | Gum was a challenge to dissolved in milk by itself. BRS needed to be added with the UA and xanthan gum. The gum still did not dissolve well. | The mouthfeel was thicker and the gel paticulates were more visible and could feel them when drinking the milk | Taste did not change; tasted like dairy milk | 266 mg UA + 0.55 g gum + 1 g BRS dissolved in 8 fl oz beverage |

Fig. 7 Cntd

| | | | | | | | | | |
|---|---|---|---|---|---|---|---|---|---|
| 4 | Whole Milk 1.5 gram BRS | 6,73 | Spindle 61 60 RPM: 4.9 cp 4.9% 30 RPM:4.0 cp 2.0% | 6,72 | Spindle 61 60RPM: 29.2cp 29.2% 30RPM: 34.6cp 30rpm 17.3% | Gum dissolved better with the extra BRS. The gel particulates were still visible | The mouthfeel was thicker and the gel paticulates were visible, but couldn't feel them when drinking | Taste did not change; tasted like dairy milk | 266 mg UA + 0.55 g gum +1.5 g BRS dissolved in 8 fl oz beverage |
| 5 | Boost Original-Vanilla | 6,8 | Spindle 61 60rpm:25.1.cp 25.1% 30rpm: 35.2 cp 17.6% | 6,77 | Spindle 62 60rpm:49.5 cp 9.7% 30rpm: 66 cp 6.6% | Some gum particulates did not dissolve well and sat on top of the sample. UA suspended in the product well | The mouthfeel was thicker and the gel particulates were visible, but couldn't feel the particulates when drinking | Taste did not change; tasted like Boost Vanilla. Nice caramel and vanilla flavor profile | 266 mg UA + 0.55 g gum +1 g BRS dissolved in 8 fl oz beverage |

Figure 7:
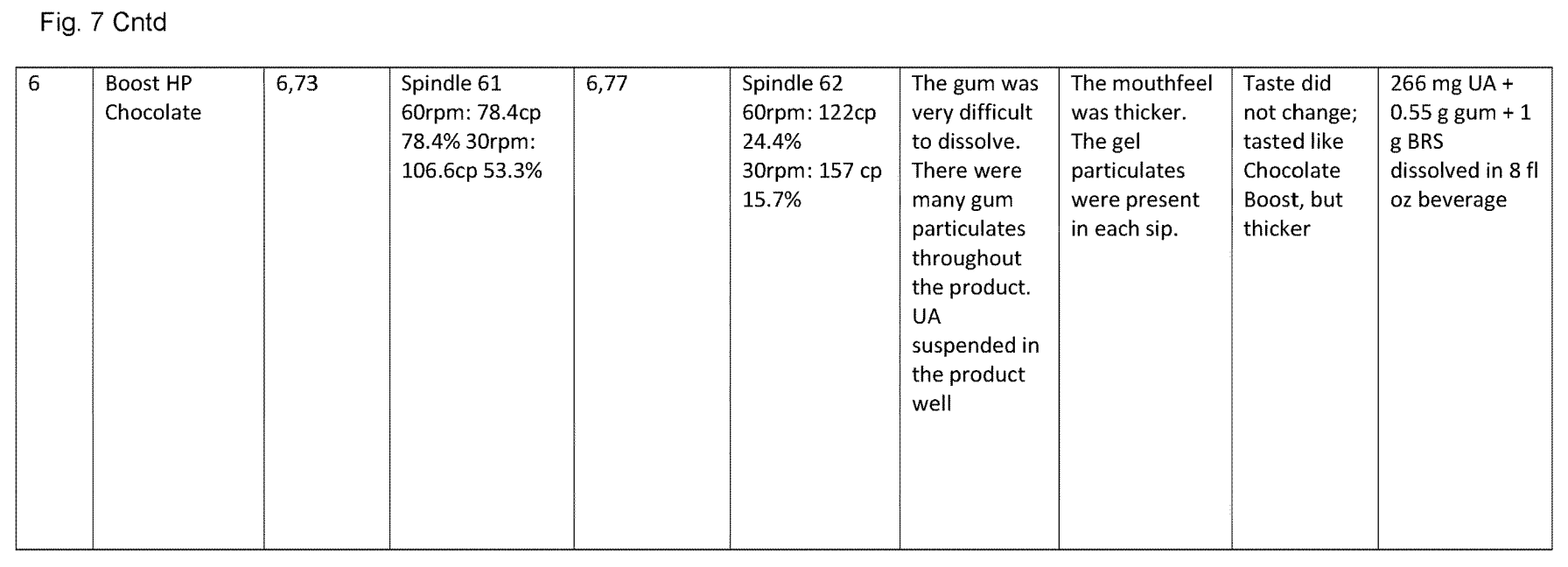

Fig. 7 Cntd

| 6 | Boost HP Chocolate | 6,73 | Spindle 61 60rpm: 78.4cp 78.4% 30rpm: 106.6cp 53.3% | 6,77 | Spindle 62 60rpm: 122cp 24.4% 30rpm: 157 cp 15.7% | The gum was very difficult to dissolve. There were many gum particulates throughout the product. UA suspended in the product well | The mouthfeel was thicker. The gel particulates were present in each sip. | Taste did not change; tasted like Chocolate Boost, but thicker | 266 mg UA + 0.55 g gum + 1 g BRS dissolved in 8 fl oz beverage |
|---|---|---|---|---|---|---|---|---|---|

Figure 7:
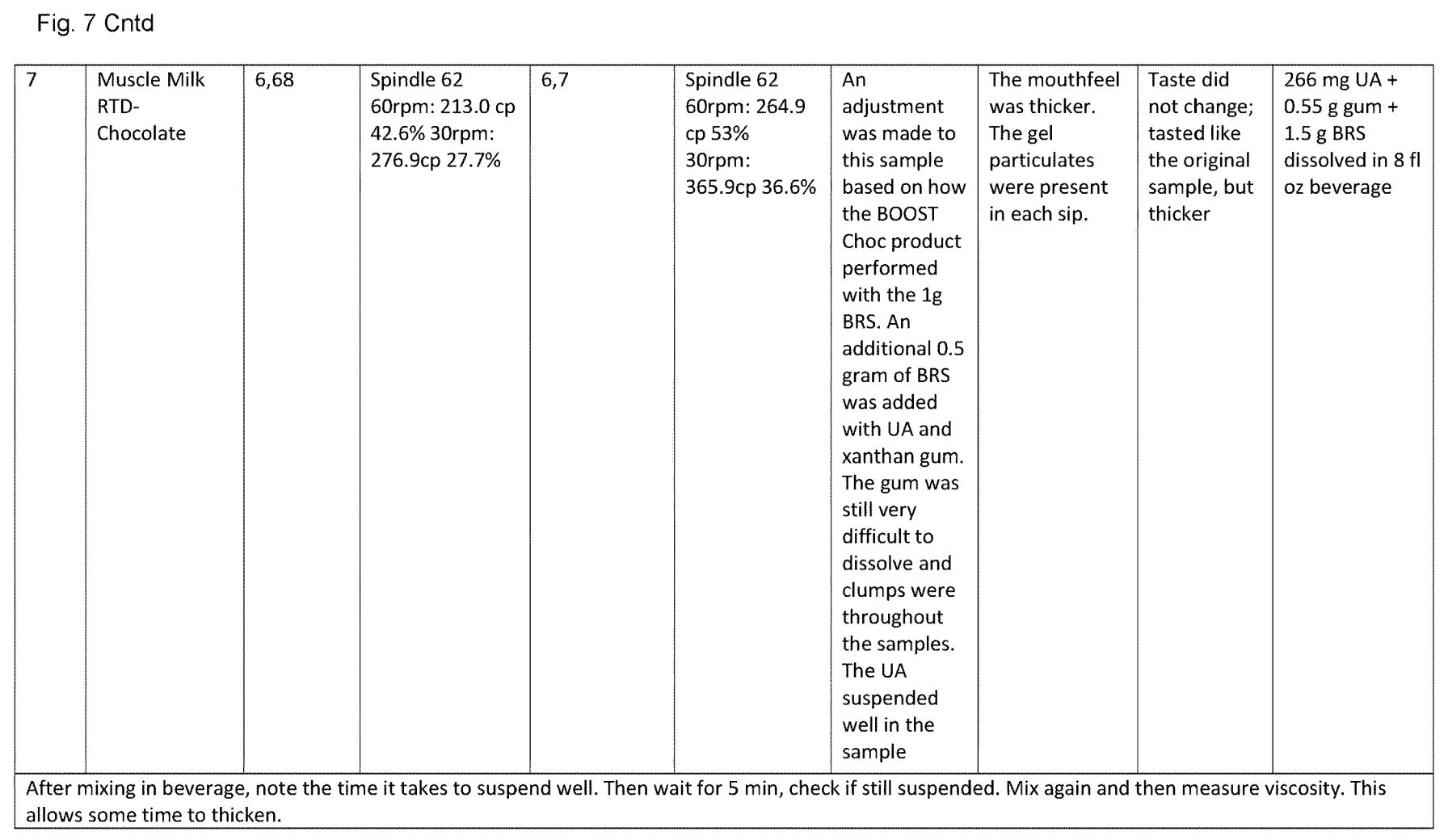

Fig. 7 Cntd

| 7 | Muscle Milk RTD-Chocolate | 6,68 | 6,7 | Spindle 62 60rpm: 213.0 cp 42.6% 30rpm: 276.9cp 27.7% | Spindle 62 60rpm: 264.9 cp 53% 30rpm: 365.9cp 36.6% | An adjustment was made to this sample based on how the BOOST Choc product performed with the 1g BRS. An additional 0.5 gram of BRS was added with UA and xanthan gum. The gum was still very difficult to dissolve and clumps were throughout the samples. The UA suspended well in the sample | The mouthfeel was thicker. The gel particulates were present in each sip. | Taste did not change; tasted like the original sample, but thicker | 266 mg UA + 0.55 g gum + 1.5 g BRS dissolved in 8 fl oz beverage |

After mixing in beverage, note the time it takes to suspend well. Then wait for 5 min, check if still suspended. Mix again and then measure viscosity. This allows some time to thicken.

Figure 8:
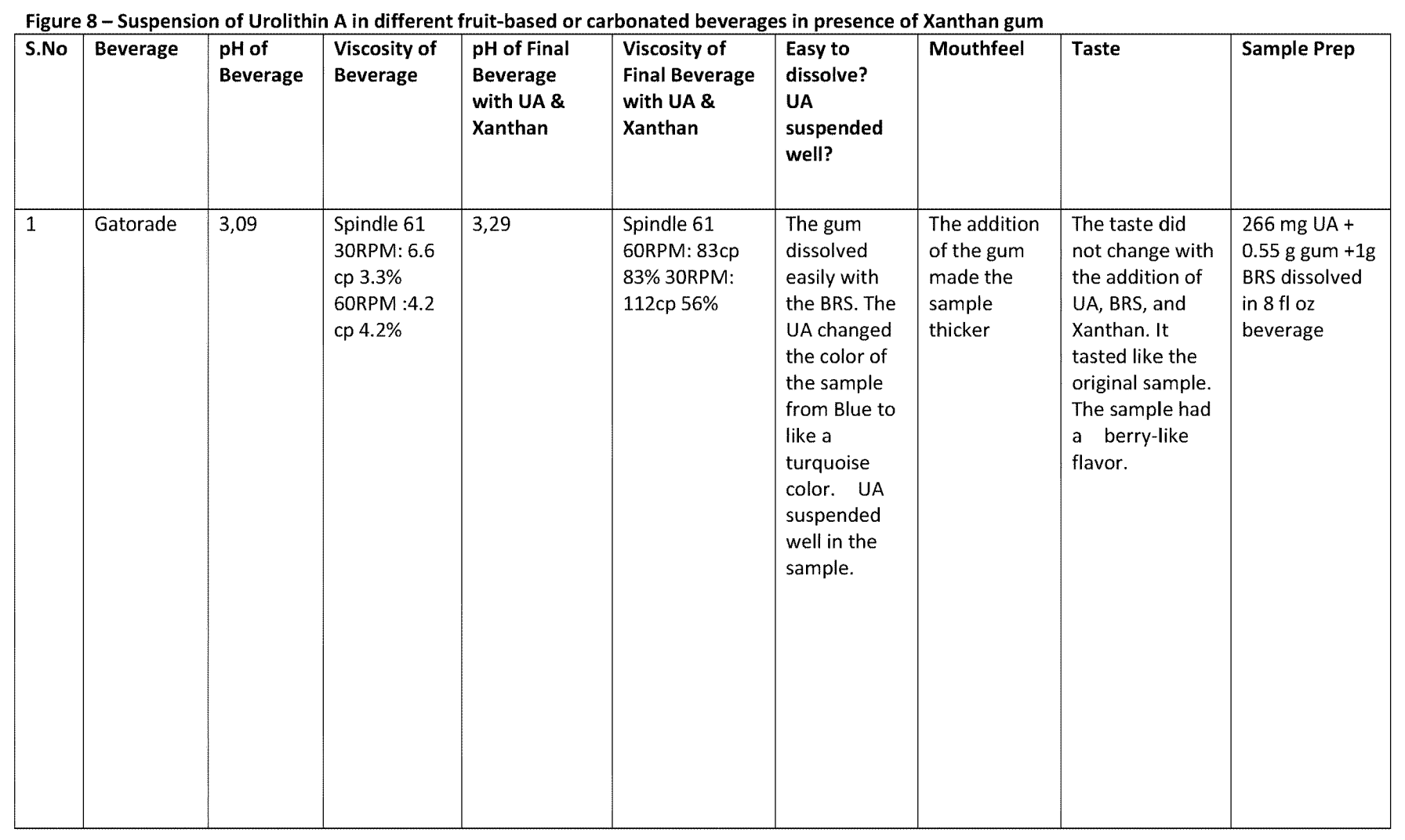

Figure 8 – Suspension of Urolithin A in different fruit-based or carbonated beverages in presence of Xanthan gum

| S.No | Beverage | pH of Beverage | Viscosity of Beverage | pH of Final Beverage with UA & Xanthan | Viscosity of Final Beverage with UA & Xanthan | Easy to dissolve? UA suspended well? | Mouthfeel | Taste | Sample Prep |
|------|----------|----------------|----------------------|----------------------------------------|-----------------------------------------------|--------------------------------------|-----------|-------|-------------|
| 1 | Gatorade | 3,09 | Spindle 61 30RPM: 6.6 cp 3.3% 60RPM :4.2 cp 4.2% | 3,29 | Spindle 61 60RPM: 83cp 83% 30RPM: 112cp 56% | The gum dissolved easily with the BRS. The UA changed the color of the sample from Blue to like a turquoise color. UA suspended well in the sample. | The addition of the gum made the sample thicker | The taste did not change with the addition of UA, BRS, and Xanthan. It tasted like the original sample. The sample had a berry-like flavor. | 266 mg UA + 0.55 g gum +1g BRS dissolved in 8 fl oz beverage |

Figure 8:
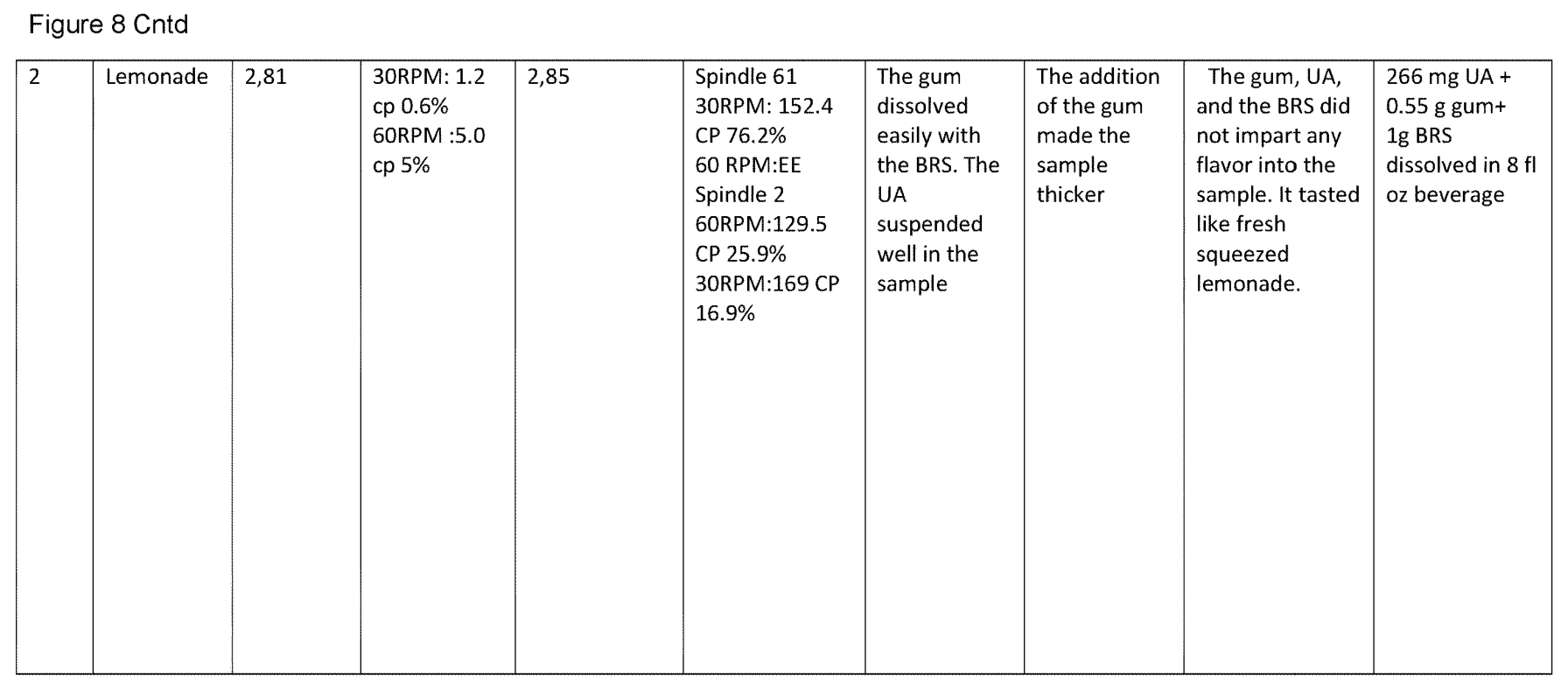

Figure 8 Cntd

| 2 | Lemonade | 2,81 | 30RPM: 1.2 cp 0.6%<br>60RPM :5.0 cp 5% | 2,85 | Spindle 61<br>30RPM: 152.4<br>CP 76.2%<br>60 RPM:EE<br>Spindle 2<br>60RPM:129.5<br>CP 25.9%<br>30RPM:169 CP<br>16.9% | The gum dissolved easily with the BRS. The UA suspended well in the sample | The addition of the gum made the sample thicker | The gum, UA, and the BRS did not impart any flavor into the sample. It tasted like fresh squeezed lemonade. | 266 mg UA + 0.55 g gum+ 1g BRS dissolved in 8 fl oz beverage |

Figure 8:
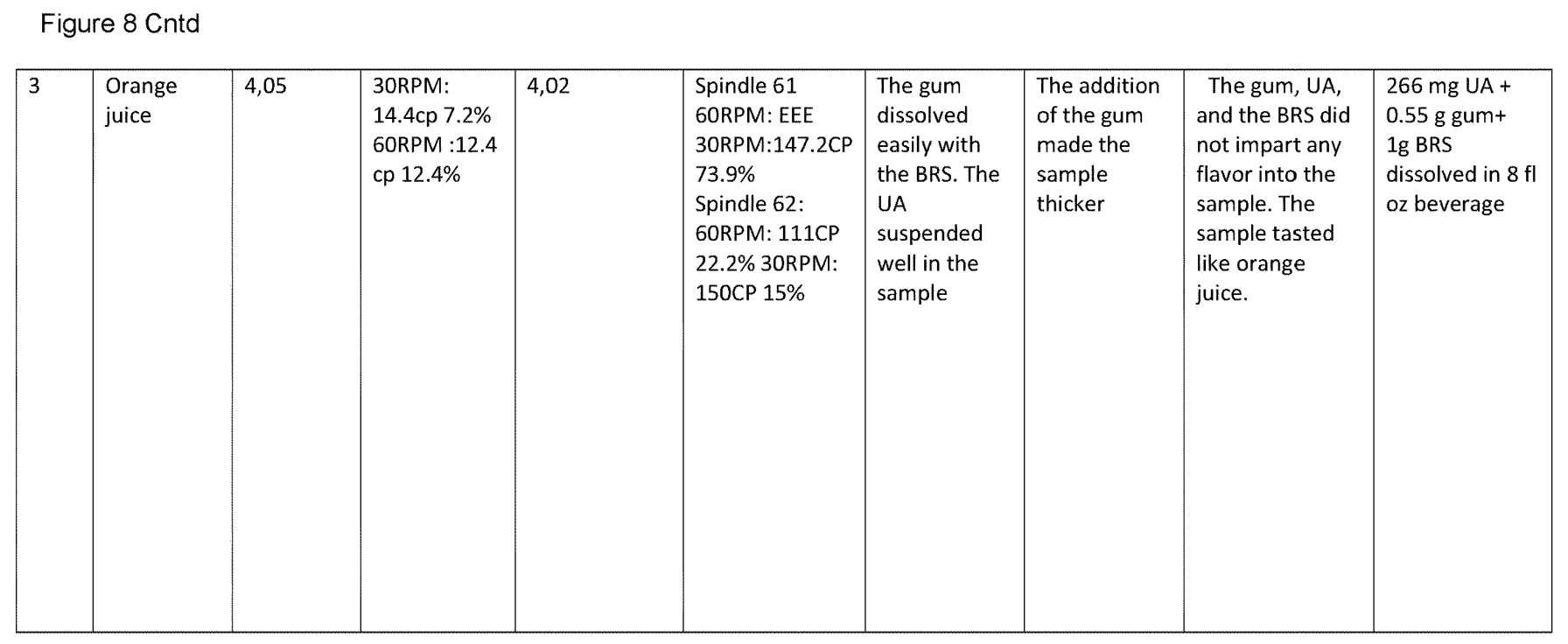

Figure 8 Cntd

| 3 | Orange juice | 4,05 | 4,02 | 30RPM: 14.4cp 7.2% 60RPM :12.4 cp 12.4% | Spindle 61 60RPM: EEE 30RPM:147.2CP 73.9% Spindle 62: 60RPM: 111CP 22.2% 30RPM: 150CP 15% | The gum dissolved easily with the BRS. The UA suspended well in the sample | The addition of the gum made the sample thicker | The gum, UA, and the BRS did not impart any flavor into the sample. The sample tasted like orange juice. | 266 mg UA + 0.55 g gum+ 1g BRS dissolved in 8 fl oz beverage |

Figure 8:
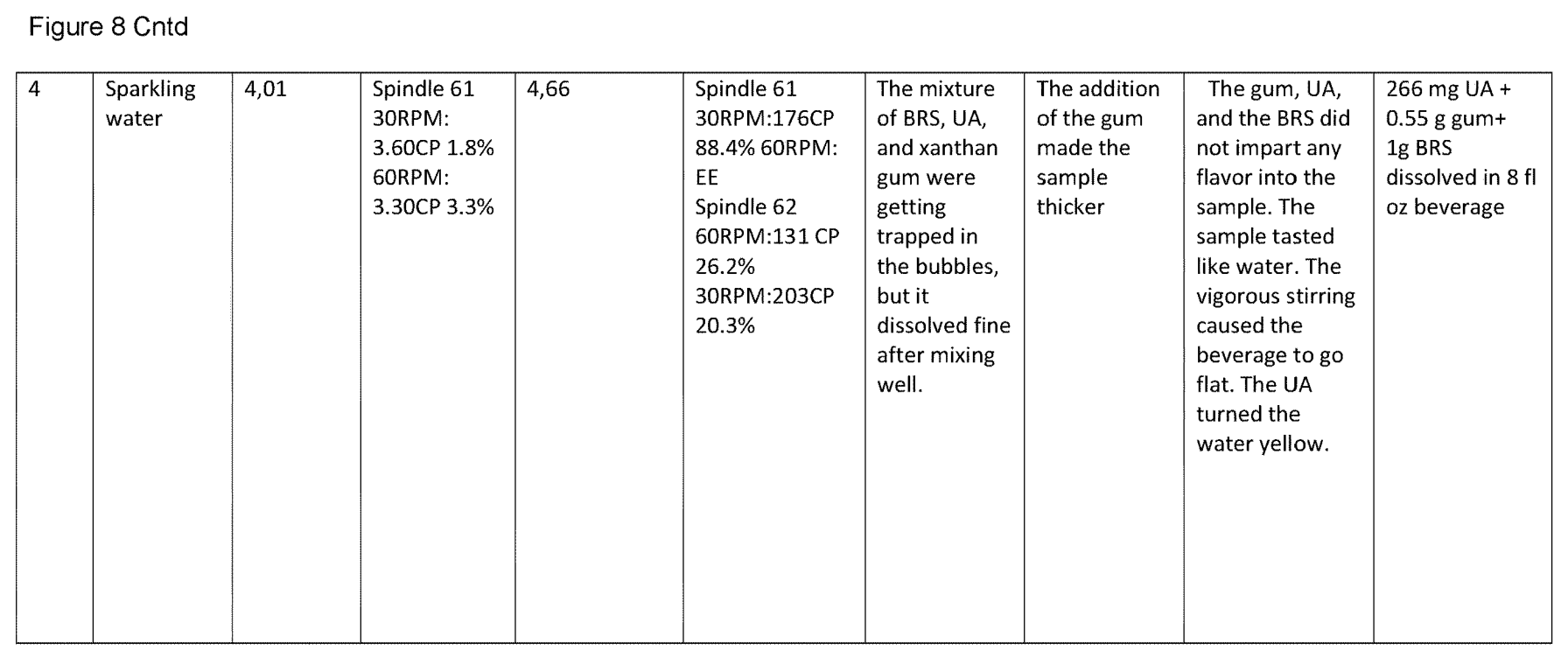

Figure 8 Cntd

| 4 | Sparkling water | 4,01 | 4,66 | Spindle 61 30RPM: 3.60CP 1.8% 60RPM: 3.30CP 3.3% | Spindle 61 30RPM:176CP 88.4% 60RPM: EE Spindle 62 60RPM:131 CP 26.2% 30RPM:203CP 20.3% | The mixture of BRS, UA, and xanthan gum were getting trapped in the bubbles, but it dissolved fine after mixing well. | The addition of the gum made the sample thicker | The gum, UA, and the BRS did not impart any flavor into the sample. The sample tasted like water. The vigorous stirring caused the beverage to go flat. The UA turned the water yellow. | 266 mg UA + 0.55 g gum+ 1g BRS dissolved in 8 fl oz beverage |

Figure 8:
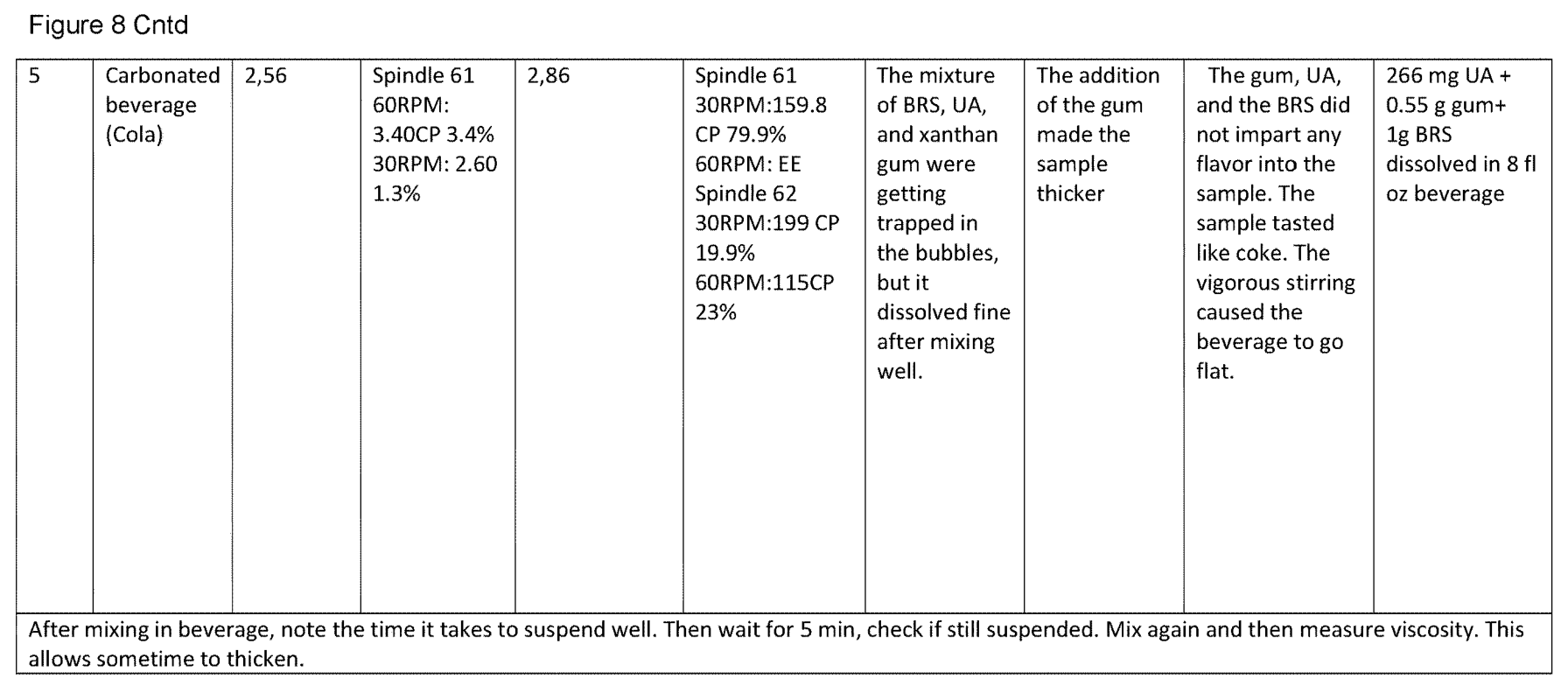

Figure 8 Cntd

| 5 | Carbonated beverage (Cola) | 2,56 | Spindle 61 60RPM: 3.40CP 3.4% 30RPM: 2.60 1.3% | 2,86 | Spindle 61 30RPM:159.8 CP 79.9% 60RPM: EE Spindle 62 30RPM:199 CP 19.9% 60RPM:115CP 23% | The mixture of BRS, UA, and xanthan gum were getting trapped in the bubbles, but it dissolved fine after mixing well. | The addition of the gum made the sample thicker | The gum, UA, and the BRS did not impart any flavor into the sample. The sample tasted like coke. The vigorous stirring caused the beverage to go flat. | 266 mg UA + 0.55 g gum+ 1g BRS dissolved in 8 fl oz beverage |

After mixing in beverage, note the time it takes to suspend well. Then wait for 5 min, check if still suspended. Mix again and then measure viscosity. This allows sometime to thicken.

Figure 9 – Effect of different levels of Xanthan gum on Urolithin A in the presence of Creatine

| S.No | Stabilizer | pH | Viscosity | Easy to dissolve? UA suspended well? | Mouthfeel | Taste | Sample Prep |
|------|-----------|------|-----------|-----------------------------------|-----------|-------|-------------|
| A-1 | Xanthan (0.6) | 4,36 | 32 | yes | ok | good | 6g FP + 8 fl oz water |
| A-2 | Xanthan (0.75) | 4,52 | 74 | yes | ok | good | 6g FP + 8 fl oz water |
| A-3 | Xanthan (0.85) | 4,54 | 92 | yes | slightly thicker | good | 6g FP + 8 fl oz water |
| US control (No creatine) | Xanthan (0.55) | 4,14 | 42 | yes | OK | good | 4g FP + 8 fl oz water |

COMPOSITIONS AND METHODS USING XANTHAN GUM TO STABILIZE AT LEAST ONE UROLITHIN IN AN AQUEOUS MATRIX

CROSS REFERENCE TO RELATED APPLICATIONS

The present application is a National Stage of International Application No. PCT/EP2021/076099, filed on Sep. 22, 2021, which claims priority to U.S. Provisional Patent Application No. 63/083,383, filed on Sep. 25, 2020, the entire contents of which are being incorporated herein by reference.

BACKGROUND

The present disclosure generally relates to compositions and methods that use xanthan gum to stabilize at least one urolithin, for example Urolithin A, in an aqueous matrix. For example, the compositions and methods disclosed herein can suspend the water-insoluble functional ingredient Urolithin A in a beverage, such as a beverage made by reconstituting a powder comprising at least a portion of Urolithin A in the beverage.

Urolithins are metabolites of ellagic acid, punicalagin (PA), punicalin (PB), tellimagrandin (TL), and other ellagitannins (Cerda, Espin et al. 2004; Cerda, Periago et al. 2005). When these metabolites are absorbed, they undergo glucuronidation, and after reaching the liver, they are further metabolized to produce glucuronides and/or sulfates. Urolithin compounds are useful in the treatment and prophylaxis of various conditions, for example by enhancement of muscle function.

SUMMARY

The present disclosure addresses the inventors' recognition that Urolithin A (UA) is insoluble in water, such that a powder containing UA as the main functional ingredient presented the challenge of keeping UA in suspension upon reconstitution of the powder with water. In this regard, UA being insoluble promotes settling of UA at the bottom of the reconstitution container almost immediately. The present disclosure includes various ways of stabilizing Urolithin A in an aqueous matrix, such that when a powder containing UA is reconstituted, the UA remains in suspension.

Additional features and advantages are described herein and will be apparent from the following Figures and Detailed Description.

BRIEF DESCRIPTION OF DRAWINGS

FIGS. 3A and 3B are tables showing the results of the first experimental example disclosed herein, where various gums were tested with Urolithin A and without citric acid.

FIGS. 4A and 4B are tables showing the results of the second experimental example disclosed herein, where various gums were tested with Urolithin A and with citric acid.

FIG. 5 is a table showing the results of a third experimental example discussed herein, where various amounts of xanthan gum were tested with Urolithin A and with citric acid.

FIGS. 6A-6D are tables showing the results of the fourth experimental example disclosed herein, where lemon-flavored or raspberry-and-pomegranate-flavored powders of urolithin A and xanthan gum were tested for stability.

FIG. 7 is a table of the suspension of Urolithin A in different milk-based beverages in presence of Xanthan gum.

FIG. 8 is a table of the suspension of Urolithin A in different fruit-based or carbonated beverages in presence of Xanthan gum.

FIG. 9 is a table of the effect of different levels of Xanthan gum on Urolithin A in the presence of Creatine.

DETAILED DESCRIPTION

Definitions

Figure 1:
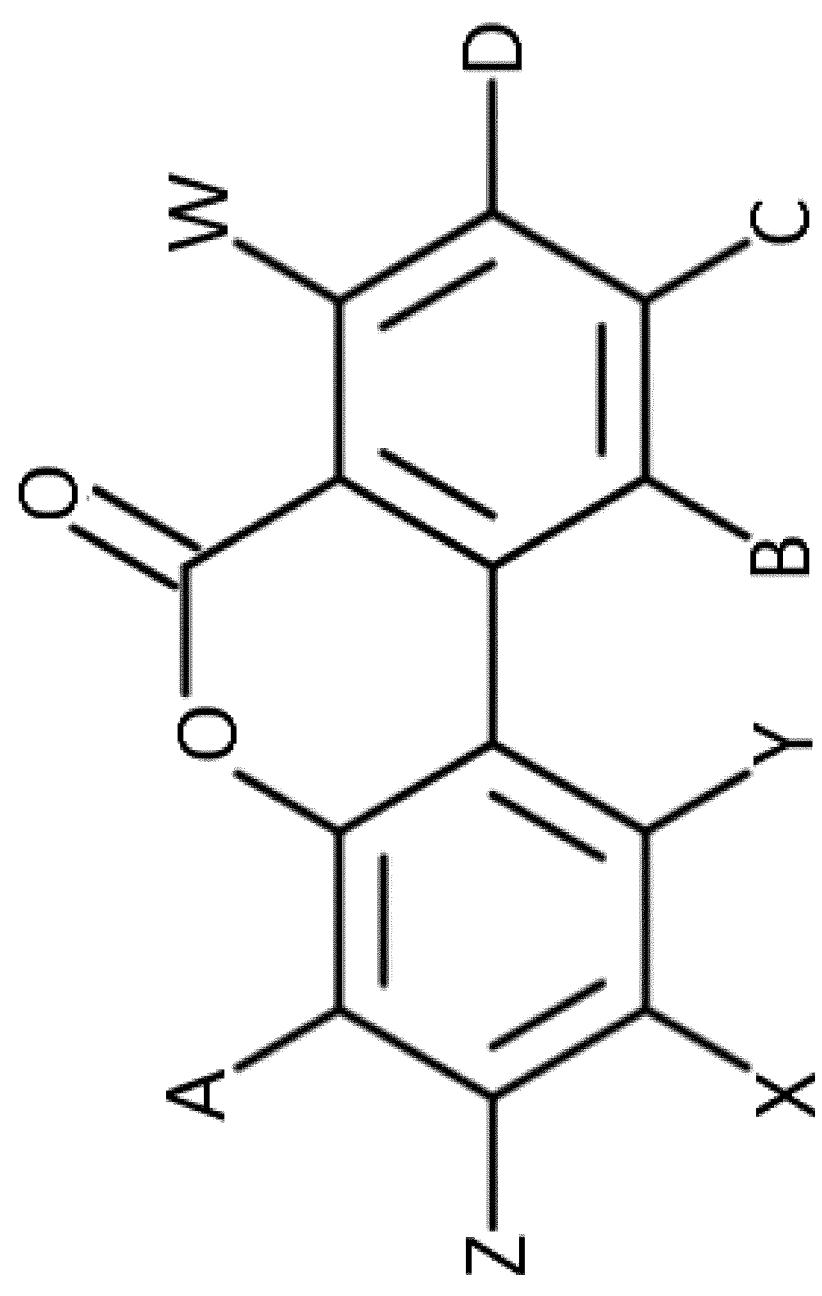
FIG. 1 depicts the structural formula for urolithins, where A, B, C and D are each independently selected from H and OH; W, X and Y are each independently selected from H and OH; and Z is selected from H and OH.

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. As used herein, "about," "approximately" and "substantially" are understood to refer to numbers in a range of numerals, for example the range of $-10\%$ to $+10\%$ of the referenced number, preferably $-5\%$ to $+5\%$ of the referenced number, more preferably $-1\%$ to $+1\%$ of the referenced number, most preferably $-0.1\%$ to $+0.1\%$ of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a urolithin" or "the urolithin" means "at least one urolithin" and includes two or more urolithins.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified.

The terms "at least one of" and "and/or" used in the respective context of "at least one of X or Y" and "X and/or Y" should be interpreted as "X," or "Y," or "X and Y." For example, "at least one of Urolithin A or Urolithin C" should be interpreted as "Urolithin A without Urolithin C," or "Urolithin C without Urolithin A," or "both Urolithin A and Urolithin C."

Where used herein, the terms "example" and "such as," particularly when followed by a listing of terms, are merely exemplary and illustrative and should not be deemed to be exclusive or comprehensive. As used herein, a condition "associated with" or "linked with" another condition means the conditions occur concurrently, preferably means that the conditions are caused by the same underlying condition, and most preferably means that one of the identified conditions is caused by the other identified condition.

A "liquid composition" may be a suspension, a solution, an emulsion, a slurry or other semi-solid liquids. The term "beverage" means a liquid composition that is intended for oral ingestion by an individual such as a human and provides at least one nutrient to the individual. A beverage optionally includes at least one of a protein, a lipid, a carbohydrate or one or more vitamins and minerals. The compositions of the present disclosure, including the many embodiments described herein, can comprise, consist of, or consist essentially of the elements disclosed herein, as well as any additional or optional ingredients, components, or elements described herein or otherwise useful in a diet.

As used herein, the term "powder" means a solid substantially homogeneous plurality of particles having a moisture content less than 5.0 wt. %, preferably a moisture content less than 4.0 wt. %, more preferably a moisture content less than 3.0 wt. %, even more preferably a moisture content less than 2.0 wt. %, and most preferably a moisture content less than 1.0 wt. %.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

As used herein, a prophylactically or therapeutically "effective amount" is an amount that prevents a deficiency, treats a disease or medical condition in an individual, or, more generally, reduces symptoms, manages progression of the disease, or provides a nutritional, physiological, or medical benefit to the individual. The relative terms "improved," "increased," "enhanced" and the like, when used to refer to the stability of the liquid compositions disclosed herein (liquid compositions comprising xanthan gum and at least one urolithin) mean that more of the at least one urolithin is in suspension relative to a composition lacking xanthan gum (e.g., replaced with another gum) but otherwise identical and reconstituted under the same conditions. As used herein, "promoting" at least one of muscle performance or mental performance refers to enhancing or inducing relative to the level before administration of the composition disclosed herein.

The term "unit dosage form," as used herein, refers to physically discrete units suitable as unitary dosages for human and animal subjects, each unit containing a predetermined quantity of the composition disclosed herein in an amount sufficient to produce the desired effect, in association with a pharmaceutically acceptable diluent, carrier or vehicle. The specifications for the unit dosage form depend on the particular compounds employed, the effect to be achieved, and the pharmacodynamics associated with each compound in the host.

A "subject" or "individual" is a mammal, preferably a human.

Embodiments

Ellagitannins and ellagic acid are compounds commonly found in foods such as pomegranates, nuts and berries. Ellagitannins are minimally absorbed in the gut themselves. Urolithins are metabolites produced by the action of mammalian, including human, gut microbiota on ellagitannins and ellagic acid. Urolithins are a class of compounds with the representative structure shown above in FIG. 1.

Any urolithin according to this structure may be used in the compositions and methods disclosed herein, and include the urolithins disclosed in U.S. Pat. No. 10,695,320 entitled "Compositions Comprising Urolithin Compounds" issued on Jun. 30, 2020 and filed as U.S. Ser. No. 15/757,293 on Aug. 26, 2016, incorporated herein in its entirety by reference, and disclosed in U.S. Patent App. Pub. No. 2018/0015069 entitled "Enhancing Autophagy or Increasing Longevity by Administration of Urolithins or Precursors Thereof" published on Jan. 18, 2018 and filed as U.S. Ser. No. 15/701,057 on Sep. 11, 2017, also incorporated herein in its entirety by reference.

Particularly suitable compounds are naturally-occurring urolithins. Thus, Z is preferably OH; and W, X and Y are preferably all H.

Figure 2:
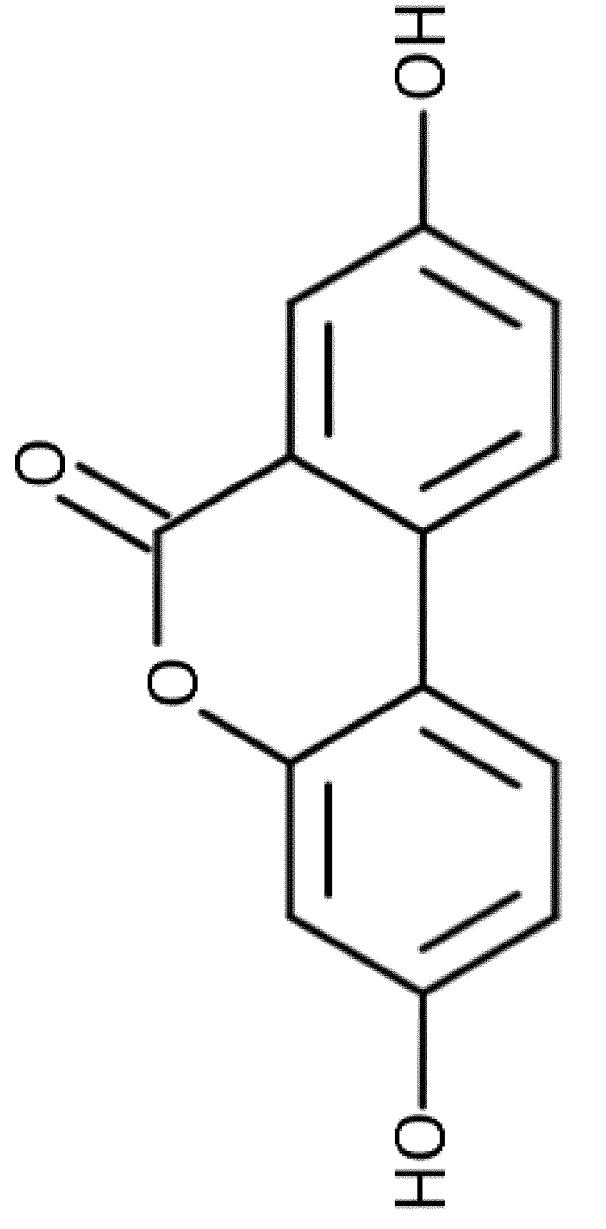
FIG. 2 depicts the structural formula for Urolithin A (UA).

Regarding particularly preferred urolithins, in Urolithin C (UC): W, X and Y are all H; and A, and B are both H; and C, D and Z are all OH. As shown in FIG. 2, in Urolithin A (UA): W, X and Y are all H, and A, B and C are all H; and D and Z are both OH. Preferably, the compositions and methods disclosed herein use at least one of Urolithin A, Urolithin B, Urolithin C or Urolithin D, even more preferably at least Urolithin A (UA).

Comparative experimental data was generated to investigate the possibility of stabilization of UA in an aqueous matrix. Further in this regard, UA was found to be sparingly soluble in oil. UA forms a good suspension in an oil matrix; but in a powder matrix, oil powders do not suspend UA in the reconstituted beverage.

EXAMPLES

Example 1: UA in Suspension

Experiments were conducted to keep UA in suspension:
1. Initially the base selected was brown rice syrup powder to which UA was added. Upon reconstitution, the UA would settle down at the base of the container.
2. UA forms a suspension in oil, so another experiment used brown rice syrup powder with canola oil powder and whey protein. This base also did not achieve effective stabilization.
3. 100% Canola oil powder base was tried, which also did not provide effective stabilization.
4. Lecithin and carrageenan were used with the expectation that they would stabilize the system, and that base also did not achieve effective stabilization.
5. MCT oil powder was used as the base but did not provide effective stabilization.

Hence, it was concluded that the oil base did not help in powder formats. UA would settle down after reconstitution into an aqueous format, and thus the approach became to use gums to increase the viscosity of the reconstituted aqueous composition to thereby keep the UA in suspension.

Specifically, different gums and concentrations of gums were investigated with UA and a filler that was brown rice syrup powder:

1. Guar gum

2. PHGG

3. Combination of guar and xanthan

4. Acacia gum

5. Gellan gum

6. FMC Gum blend

7. Xanthan gum

Table 1 (below) sets forth the formulations of the samples testing various gums with UA. FIGS. 3A and 3B set forth the results from these samples.

TABLE 1

| Ingredient | Quantity/ 100 g | Base for 4 g svg |
|---|---|---|
| Brown rice syrup powder | 29 | 1.16 |
| Urolithin A | 6.65 | 0.266 |
| BASE (no acid) | 35.65 | 1.426 |
| To 1.43 g Base add 0.55 g Gum and mix well. Then add to 8 fl oz of water | | Total 7 prototypes |
| 1. Gum xanthan 80mesh | | 0.55 |
| 2. Acacia Gum | | 0.55 |
| 3. Gellan Gum | | 0.55 |
| 4. Guar Gum | | 0.55 |
| 5. PHGG | | 0.55 |
| 6. FMC Gum Blend | | 0.55 |
| 7. blend of guar and xanthan | | 0.5 g guar + 0.05 g xanthan |

Some embodiments of the compositions disclosed herein include fruit flavor and thus citric acid. Thus, the pH would be low in such compositions, and preferably protein can be excluded from the compositions so that xanthan gum was stable and did not form a gel. Table 2 (below) sets forth the formulations of the samples testing various gums with UA and citric acid. FIGS. 4A and 4B sets forth the results from these samples.

TABLE 2

| Ingredient | Quantity/ 100 g | Base for 4 g svg |
|---|---|---|
| Brown rice syrup powder | 29 | 1.16 |
| Citric acid anhydrous | 20 | 0.8 |
| Urolithin A | 6.65 | 0.266 |
| BASE | 55.65 | 2.226 |
| To 2.23 g base add 0.55 g Gum and mix well. Then add to 8 fl oz of water | | Total 7 prototypes |
| 1. Gum xanthan 80mesh | | 0.55 |
| 2. Acacia Gum | | 0.55 |
| 3. Gellan Gum | | 0.55 |
| 4. Guar Gum | | 0.55 |
| 5. PHGG | | 0.55 |

TABLE 2-continued

| | |
|---|---|
| 6. FMC Gum Blend | 0.55 |
| 7. blend of guar and xanthan | 0.5 g guar + 0.05 g xanthan |

For each sample, after mixing the powder with water, five minutes elapsed, then the suspension was mixed again, and then viscosity was measured. Out of the various experiments, xanthan gum provided the best solution of not only keeping UA in suspension but also the desired viscosity, easily dissolved, and no off taste/odor to the product.

A range of xanthan gum amounts were then studied (Table 3 and FIG. 5). In a particular non-limiting example, the final usage rate in the powder was 0.55 g xanthan/serving (4 g serving size) or at 13.75 wt. % in the powder. A range from 0.5 g-0.65 g xanthan/serving (12.5-16.25 wt. % in finished powder by dry weight) was effective, with good mouthfeel and thickness and also could suspend UA well upon reconstitution of 4 g finished product in 8 fl. oz. of water.

TABLE 3

| Ingredient | Quantity/ 100 g | Quantity/ 4 g svg (13.75% xanthan) | Quantity/ 4 g svg (11.25% xanthan) | Quantity/ 4 g svg (16.25% xanthan) |
|---|---|---|---|---|
| Glucose syrup rice powder 28-32 DE | 29 | 1.16 | 1.26 | 1.06 |
| Citric acid anhydrous | 20 | 0.8 | 0.8 | 0.8 |
| Gum xanthan 80mesh | 13.75 | 0.55 | 0.45 | 0.65 |
| Urolithin A | 6.65 | 0.266 | 0.266 | 0.266 |
| TriMagnesium Phosphate Pentahydrate | 12.5 | 0.5 | 0.5 | 0.5 |
| Flavor & color | 14.75 | 0.059 | 0.059 | 0.059 |
| sweetener | 3.35 | 0.134 | 0.134 | 0.134 |

Then stability was further tested in an additional experiment, and FIGS. 6A-6D sets forth the results. Specifically, a lemon-flavored powder of Urolithin A and xanthan gum (FIGS. 6A and 6B) and a raspberry-and-pomegranate flavoured powder of Urolithin A and xanthan gum (FIGS. 6C and 6D) were tested by mixing 4 g of the powder in 8 fl. oz. water and stirred well for 4 minutes, and the solution thickens and the urolithin is suspended well; the reconstituted sample was allowed to stand for 5 minutes at room temperature; and the experiment was performed in duplicates for each flavor. As shown in the results, the reconstituted urolithin remained suspended well even after 5 minutes of standing at room temperature.

Example 2: Urolithin Stabilized in Reconstituted Milk-Based Beverages with Xanthan Gum Urolithin A can be stabilized in reconstituted beverages using xanthan gum. Experiments were conducted to see that stabilization of Urolithin A using xanthan gum and some bulking agent (brown rice syrup powder) in other milk based and fruit-based/carbonated beverages.

Experiment was also conducted to see the stabilization of Urolithin A in presence of Creatine using Xanthan gum and some bulking agent (brown rice syrup powder) in both milk and fruit-based/carbonated beverages.

For the milk-based beverages FIG. 7 shows the different experiments along with the observations.

The results showed that it was possible to add Urolithin A and Xanthan gum along with bulking agent to milk based beverages. There was no impact on taste with the addition of Urolithin A, brown rice syrup powder, and creatine. However, there was some impact on mouthfeel which was improved with higher levels of brown rice syrup powder as bulking agent. The gum did form some gel-like particles which changed the mouthfeel to some extent. The experiment was done with whole milk, skim milk, Boost Vanilla RTD, Boost Chocolate RTD and Muscle Milk (Chocolate).

Example 3: Urolithin Stabilized in Fruit Based or Carbonated Beverages with Xanthan Gum The results in FIG. 8 showed that it was possible to add Urolithin A and Xanthan gum along with bulking agent to fruit based or carbonated beverages. Urolithin A, the bulking agent, and Xanthan gum did not have an impact on taste, but the addition of creatine had a slight impact on taste. The sourness seemed to be mellowed. The thickness of the product increased and so did the mouthfeel. Urolithin A had an impact on the color. In case of carbonated beverages, due to stirring and thickening while stirring, some carbonation was lost. This study was conducted on Gatorade, lemonade, orange juice, sparkling water, and cola.

Example 4: Urolithin Stabilized in Milk-Based Beverages with Xanthan Gum and Creatine Creatine is a natural substance produced by our body by conversion of amino acids glycine, arginine and methionine contained in our food. Additional creatine can also be directly absorbed through our food, especially from fish and meat. Those who do not have a balanced diet and eat little fish and meat likely have lower levels of creatine in their bodies.

Athletes, needing additional creatine for muscle growth and faster recovery times after strenuous workouts, can benefit from creatine supplementation in the form dietary supplements. Food supplements containing creatine have been shown to have positive effects on the energy supply to muscle cells during and between exercise performances.

Creatine monohydrate dissolves somewhat slowly in cold water or other cold drinks. It is recommended to take creatine with sugary drinks (e.g., grape juice) or with a meal because the muscles of your body can absorb creatine more easily when insulin is present. FIG. 9 describes the effect of different levels of Xanthan gum on Urolithin A in the presence of Creatine.

The creatine monohydrate that was used for the study was from Alzchem (brand name Creapure).

The formulations were developed with 250 mg Urolithin A and 1.5 g Creatine per serving of powder finished product (6 g serving). Reconstitution was 6 g serving mixed in 8 fl. Oz of water. Overage for creatine was 15%.

Xanthan gum was used to stabilize this formulation and ranged from 0.6-0.85 g/svg of 6 g (10-14.17%).

The experiment also showed similar observations as above in Example 2 with addition of Creatine but was thicker due to the gum thickening over time.

Example 5: Urolithin Stabilized in Fruit Based/Carbonated Beverages with Xanthan Gum and Creatine The creatine monohydrate that was used for the study was from Alzchem (brand name Creapure).

The formulations were developed with 250 mg Urolithin A and 1.5 g Creatine per serving of powder finished product (6 g serving). Reconstitution was 6 g serving mixed in 8 fl. Oz of water. Overage for creatine was 15%.

Xanthan gum was used to stabilize this formulation and ranged from 0.6-0.85 g/svg of 6 g (10-14.17%).

The experiment also showed similar observations as above in Example 3 with addition of Creatine but was thicker due to the gum thickening over time.

Accordingly, various embodiments in the present disclosure include a powder comprising xanthan gum and at least one urolithin. Some embodiments include a liquid for oral consumption (e.g., a beverage) comprising xanthan gum and at least one urolithin, for example a liquid for oral consumption made by reconstituting any of the powders disclosed herein. Some embodiments further include creatine.

Powders are commonly used for the supply of nutritional and medical compositions. Powders have the advantage that multiple doses can be provided in a simple container, and doses of various sizes can be used from the same supplied container. Powders generally have good storage properties. The powders disclosed herein may, in addition to the xanthan gum and the at least one urolithin, also contain fillers or excipients conventional in the art. The excipients can, for example, provide a shelf-life, flavour and moisture resistance such that the composition has an acceptable taste, an attractive appearance and good storage stability.

Optionally the powder or the liquid for oral consumption can be provided in a unit dosage form that contains (i) a prophylactically or therapeutically effective amount of the at least one urolithin and (ii) an amount of the xanthan gum effective to maintain the majority of the at least one urothilin in suspension after reconstitution of the powder. For example, the amount of the xanthan gum in the unit dosage form can be effective to maintain the majority of the at least one urothilin in suspension for at least five minutes after reconstitution of 4 g of the powder in 8 fl. oz. of water at about 20° C.

In some embodiments, the present disclosure provides a method of producing such a powder and a method of producing such a liquid for oral consumption (e.g., a beverage). The method can comprising admixing at least one urolithin, for example in powder form, with xanthan gum, for example in powder form, to form a powder formulated for reconstitution in a liquid for oral consumption.

In some embodiments, the present disclosure provides methods of medical and/or non-medical treatment in which such a liquid for oral consumption (e.g., a beverage) are orally administered to an individual, such as a mammal, e.g., a human, optionally by reconstituting the powder in a liquid such as water before the administration.

In some embodiments, the composition is administered to an individual having impaired physical performance, impaired endurance capacity, and/or impaired muscle function. Improved muscle function can be particularly beneficial in elderly subjects with reduced muscle function as a result of an age-related condition. For example, a subject who may benefit from improved muscle function may experience a decline in muscle function which then leads to pre-frailty and frailty. Such subjects may not necessarily experience muscle wastage in addition to their decline in muscle function. Some subjects do experience both muscle wasting and a decline in muscle function, for example subjects with sarcopenia. The composition may enhance muscle performance in a subject who is frail or pre-frail.

In some embodiments, the powder or the liquid for oral consumption preferably does not contain at least one of guar gum, partially hydrolyzed guar gum (PHGG), acacia gum, gellan gum, cellulose, or modified cellulose; more preferably does not contain any of these gums; and in a particularly preferred embodiment, the xanthan gum is the only gum in the powder or the liquid for oral consumption.

Optionally the powder can include a filler, such as one or more carbohydrates, for example one or more of maltodextrin, hydrolyzed or modified starch or cornstarch, glucose polymers, corn syrup, corn syrup solids, rice-derived carbohydrates, glucose, fructose, lactose, high fructose corn syrup, tapioca dextrin, isomaltulose, sucromalt, maltitol powder, glycerin, fructooligosaccharides, soy fiber, corn fiber, guar gum, konjac flour, polydextrose, honey, sugar alcohols (e.g., maltitol, erythritol, sorbitol), and combinations thereof.

Additionally or alternatively, a sweetener may be included in the powder. High potency non-nutritive carbohydrate sweetening agents may be used, for example selected from aspartame, sucralose, potassium acelsufame, saccharin, cyclamates, *Stevia*, thaumatin and mixtures thereof.

Optionally, the powder can include a flavoring, such as a fruit flavor. Non-limiting examples of suitable flavorings include strawberry, raspberry, blueberry, apricot, pomegranate, peach, pineapple, lemon, orange and apple. Generally, fruit flavorings include one or more of fruit extract, fruit preserve or fruit puree, with any of a combination of sweeteners, starch, stabilizer, natural and/or artificial flavors, colorings, preservatives, and citric acid or other suitable acid to control the pH.

Optionally, the powder can include a protein, such as protein from one or more of milk, animal, cereal or vegetable, for example one or more of intact pea protein, intact pea protein isolates, intact pea protein concentrates, milk protein isolates, milk protein concentrates, casein protein isolates, casein protein concentrates, whey protein concentrates, whey protein isolates, sodium or calcium caseinates, whole cow's milk, partially or completely defatted milk, soy protein isolates and soy protein concentrates, and combinations thereof.

In some embodiments, the powder can include a flavor, such as a fruit flavor comprising citric acid. Preferably, only one of protein or citric acid is included in the powder.

In some embodiments, the powder consists essentially of or consists of xanthan gum, at least one urolithin, optionally a filler, and optionally citric acid.

The at least one urolithin can be provided by any of the compositions disclosed by WO2012/088519 entitled "Compositions and Methods for Improving Mitochondrial Function and Treating Neurodegenerative Diseases and Cognitive Disorders" (also published as U.S. Pat. No. 9,872,850), WO2014/004902 entitled "Enhancing Autophagy or Increasing Longevity by Administration of Urolithins or Precursors Thereof" (also published as U.S. Pat. App. Publ. No. 2014/0018415), WO2017/036992 entitled "Compositions Comprising Urolithin Compounds" and WO2017/036993 entitled "Compositions Comprising an Urolithin Compound," each incorporated herein by reference in its entirety. For example, xanthan gum can be added to any of these compositions in powder form.

The at least one urolithin can be administered in a total amount of about 0.2-150 milligram (mg) of urolithin per kilogram (kg) of body weight of the subject. Preferably, the at least one urolithin is administered in a daily dose equal or equivalent to 2-120 mg of urolithin per kg body weight of the subject, more preferably 4-90 mg of urolithin per kg body weight of the subject, most preferably 8-30 mg of urolithin per kg body weight of the subject. Any given dose may be given as a single dose or as divided doses.

In an embodiment, the at least one urolithin is administered in a dose sufficient to achieve a peak serum level of at least 0.001 micromolar (µM), preferably at least 0.01 µM, more preferably at least 0.1 µM, most preferably at least 1 µM, at least 5 µM or at least 10 µM. In an embodiment, the at least one urolithin is administered in a dose sufficient to achieve a sustained serum level of at least 0.001 micromolar (µM), preferably at least 0.01 µM, more preferably at least 0.1 µM, most preferably at least 1 µM, at least 5 M or at least 10 µM. The sustained serum level can be measured using any suitable method, for example, high pressure liquid chromatography (HPLC) or HPLC-MS.

Preferably, the at least one urolithin is micronized for more rapid dispersion or dissolution. If micronized urolithin is used, then preferably the $D_{50}$ is under 100 m, i.e., 50% by mass of the at least one urolithin has a particle diameter size under 100 µm. More preferably, the at least one urolithin has a $D_{50}$ of under 75 µm, for example under 50 m, for example under 25 µm, for example under 20 µm, for example under 10 µm. More preferably, the at least one urolithin has a $D_{50}$ in the range 0.5 to 50 µm, for example 0.5 to 20 µm, for example 0.5 to 10 µm, for example 1.0 to 10 µm, for example 1.5 to 7.5 µm, for example 2.8 to 5.5 µm. Preferably, the at least one urolithin has a $D_{90}$ size under 100 µm. More preferably, the at least one urolithin has a $D_{90}$ size under 75 µm, for example under 50 µm, for example under 25 µm, for example under 20 µm, for example under 15 µm. The at least one urolithin preferably has a $D_{90}$ in the range 5 to 100 µm, for example 5 to 50 µm, for example 5 to 20 µm, for example 7.5 to 15 µm, for example 8.2 to 16.0 µm.

Preferably, the at least one urolithin has a $D_{10}$ in the range 0.5-1.0 µm. Preferably, the at least one urolithin has a $D_{90}$ in the range 8.2 to 16.0 µm, a $D_{50}$ in the range 2.8 to 5.5 µm and a $D_{10}$ in the range 0.5 to 1.0 µm.

Micronization can be achieved by a method selected from the group consisting of compressive force milling, hammer-milling, universal or pin milling, and jet milling such as spiral jet milling or fluidized-bed jet milling. Jet milling is particularly preferred.

In view of the foregoing disclosures, an aspect of the present disclosure is a powder comprising xanthan gum and further comprising at least one compound of Formula (I) or a salt thereof as shown in FIG. 1, wherein A, B, C and D are each independently selected from H and OH; W, X and Y are each independently selected from H and OH; and Z is selected from H and OH.

In a preferred embodiment, the at least one urolithin is selected from the group consisting of urolithin A, urolithin B, urolithin C, urolithin D, and mixtures thereof. Most preferably, the at least one urolithin comprises urolithin A.

The xanthan gum can be about 12.5 wt. % to about 16.25 wt. % of the powder by dry weight. Optionally, the xanthan gum is the only gum in the powder. The powder can consist essentially of the xanthan gum, the at least one urolithin, optionally a filler, and optionally citric acid.

In another aspect of the present disclosure, a method of making a liquid composition for oral consumption comprises reconstituting any of the powders disclosed herein in a liquid. The liquid can be water, and the liquid composition can be a beverage. Preferably, the majority of the at least one urolithin is in suspension in the beverage at least 5 minutes after the reconstituting when about 4 g of the powder is reconstituted in 8 fl. oz. of water at 20° C.

In yet another aspect of the present disclosure, a liquid composition for oral consumption is made by reconstituting any of the powders disclosed herein.

Another aspect of the present disclosure is a liquid composition for oral consumption comprising xanthan gum and further comprising at least one urolithin.

Yet another aspect of the present disclosure is a method of preventing or treating a disease or condition selected from the group consisting of metabolic syndrome, reduced metabolic rate, metabolic stress, cardiovascular disease, sarcopenia, muscle degenerative disease, Duchenne muscular dystrophy, alcoholic liver disease, nonalcoholic fatty liver disease, drug-induced liver injury, drug-induced cravings, anaemia disorders, al-antitrypsin deficiency, ischemia/reperfusion injury, inflammation, aging of the skin, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, multiple sclerosis, anxiety disorder, ulceration, amyotrophic lateral sclerosis, age-related macular degeneration, cancer, cognitive disorder, stress, mood disorder, and combinations thereof. The method comprises orally administering a prophylactically or therapeutically effective amount of a beverage comprising xanthan gum and further comprising at least one urolithin to a subject having the disease or condition or at risk of the disease or condition.

In this method, the subject can be a human. Preferably, the method comprises reconstituting a powder that comprises at least a portion of the xanthan gum and at least a portion of the at least one urolithin, wherein the powder is reconstituted in a liquid to form the beverage before the administering of the beverage to the subject.

Yet another aspect of the present disclosure is a method of achieving at least one result selected from the group consisting of (i) managing body weight, (ii) promoting at least one of muscle performance or mental performance, (iii) maintaining at least one of muscle function, strength or stamina, (iv) preventing muscle decline with age, (v) maintaining or enhancing mitochondrial function (mitophagy), and (vi) supporting or promoting at least one of cellular renewal or cellular protection. The method comprises orally administering an effective amount of a beverage comprising xanthan gum and further comprising at least one urolithin to a subject in need thereof.

In this method, the subject can be a human, for example a human who has an age of at least 50 years, such as an elderly human. Preferably, the method comprises reconstituting a powder that comprises at least a portion of the xanthan gum and at least a portion of the at least one urolithin, wherein the powder is reconstituted in a liquid to form the beverage before the administering of the beverage to the subject.

Yet another aspect of the present disclosure is a method of making a powder formulated to be reconstituted in a liquid to form a liquid composition. The method comprises admixing xanthan gum and at least one urolithin. Preferably, one or both of the xanthan gum and the at least one urolithin are in powder form during the admixing.

Yet another aspect of the present disclosure is a method of enhancing stability of at least one urolithin in a liquid composition for oral consumption. At least a portion of the at least one urolithin is present in a powder formulated to be reconstituted in a liquid to form the liquid composition. The method comprises incorporating xanthan gum in the powder.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A powder comprising xanthan gum and further comprising at least one compound of Formula (I) or a salt thereof:

(I)

wherein A, B, C and D are each independently selected from H and OH; W, X and Y are each independently selected from H and OH; and Z is selected from H and OH.

2. The powder of claim 1, wherein the at least one compound is at least one urolithin selected from the group consisting of urolithin A, urolithin B, urolithin C, urolithin D, and mixtures thereof.

3. The powder of claim 1, wherein the at least one compound is urolithin A.

4. The powder of claim 1, wherein the xanthan gum is about 12.5 wt. % to about 16.25 wt. % of the powder by dry weight.

5. The powder of claim 1, wherein the xanthan gum is the only gum in the powder.

6. The powder of claim 1, consisting essentially of the xanthan gum, the at least one compound, wherein the compound is at least one urolithin.

7. The powder of claim 1, further comprising creatine.

8. A method of reducing risk and/or severity of or treating a disease or condition selected from the group consisting of metabolic syndrome, reduced metabolic rate, metabolic stress, cardiovascular disease, sarcopenia, muscle degenerative disease, Duchenne muscular dystrophy, alcoholic liver disease, nonalcoholic fatty liver disease, drug-induced liver injury, drug-induced cravings, anaemia disorders, al-antitrypsin deficiency, ischemia/reperfusion injury, inflammation, aging of the skin, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, multiple sclerosis, anxiety disorder, ulceration, amyotrophic lateral sclerosis, age-related macular degeneration, cancer, cognitive disorder, stress, mood disorder, and combinations thereof, the method comprising:

orally administering an effective amount of a beverage reconstituted from a powder comprising xanthan gum and further comprising at least one compound of Formula (I) or a salt thereof:

(I)

13 wherein A, B, C and D are each independently selected from H and OH; W, X and Y are each independently selected from H and OH; and Z is selected from H and OH to a subject in need thereof having the disease or condition or at risk of the disease or condition.

9. The method of claim 8, wherein the subject is a human.

10. A method of achieving at least one result selected from the group consisting of (i) managing body weight, (ii) promoting at least one of muscle performance or mental performance, (iii) maintaining at least one of muscle function, strength or stamina, (iv) reducing risk and/or severity of muscle decline with age, (v) maintaining or enhancing mitochondrial function (mitophagy), and (vi) supporting or promoting at least one of cellular renewal or cellular protection, the method comprising:

orally administering an effective amount of a powder comprising xanthan gum and further comprising at least one compound of Formula (I) or a salt thereof:

(I)

14 wherein A, B, C and D are each independently selected from H and OH; W, X and Y are each independently selected from H and OH; and Z is selected from H and OH to a subject in need thereof.

11. The method of claim 10, wherein the subject is a human.

12. The method of claim 11, wherein the human has an age of at least 50 years.

13. The method of claim 8, wherein the disease or condition selected from the group consisting of metabolic syndrome, reduced metabolic rate, metabolic stress, cardiovascular disease, sarcopenia, muscle degenerative disease, Duchenne muscular dystrophy, alcoholic liver disease, non-alcoholic fatty liver disease, drug-induced liver injury, drug-induced cravings, anaemia disorders, $\alpha 1$-antitrypsin deficiency, ischemia/reperfusion injury, inflammation, aging of the skin, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, multiple sclerosis, anxiety disorder, ulceration, amyotrophic lateral sclerosis, age-related macular degeneration, cognitive disorder, stress, mood disorder, and combinations thereof.

* * * * *